United States Patent [19]

Chakrabarty

[11] 4,259,444

[45] Mar. 31, 1981

[54] MICROORGANISMS HAVING MULTIPLE COMPATIBLE DEGRADATIVE ENERGY-GENERATING PLASMIDS AND PREPARATION THEREOF

[75] Inventor: Ananda M. Chakrabarty, Latham, N.Y.

[73] Assignee: General Electric Company, Schenectady, N.Y.

[21] Appl. No.: 260,563

[22] Filed: Jun. 7, 1972

[51] Int. Cl.³ .............................................. C12N 15/00
[52] U.S. Cl. .................................. 435/172; 435/253; 435/264; 435/281; 435/820; 435/875; 435/877
[58] Field of Search .............. 195/28 R, 1, 3 H, 3 R, 195/96, 78, 79, 112; 435/172, 253, 264, 820, 281, 875, 877

[56] References Cited

PUBLICATIONS

Annual Review of Microbiology vol. 26 Annual Review Inc. 1972 pp. 362–368.
Journal of Bacteriology vol. 106 pp. 468–478 (1971).
Bacteriological Reviews vol. 33 pp. 210–263 (1969).

*Primary Examiner*—R. B. Penland
*Attorney, Agent, or Firm*—Leo I. MaLossi; James C. Davis, Jr.

[57] ABSTRACT

Unique microorganisms have been developed by the application of genetic engineering techniques. These microorganisms contain at least two stable (compatible) energy-generating plasmids, these plasmids specifying separate degradative pathways. The techniques for preparing such multi-plasmid strains from bacteria of the genus Pseudomonas are described. Living cultures of two strains of Pseudomonas (*P. aeruginosa* [NRRL B-5472] and *P. putida* [NRRL B-5473]) have been deposited with the United States Department of Agriculture, Agricultural Research Service, Northern Marketing and Nutrient Research Division, Peoria, Ill. The *P. aeruginosa* NRRL B-5472 was derived from *Pseudomonas aeruginosa* strain 1c by the genetic transfer thereto, and containment therein, of camphor, octane, salicylate and naphthalene degradative pathways in the form of plasmids. The *P. putida* NRRL B-5473 was derived from *Pseudomonas putida* strain PpG1 by genetic transfer thereto, and containment therein, of camphor, salicylate and naphthalene degradative pathways and drug resistance factor RP-1, all in the form of plasmids.

18 Claims, 2 Drawing Figures

MICROORGANISMS HAVING MULTIPLE COMPATIBLE DEGRADATIVE ENERGY-GENERATING PLASMIDS AND PREPARATION THEREOF

BACKGROUND OF THE INVENTION

The terminology of microbial genetics is sufficiently complicated that certain definitions will be particularly useful in the understanding of this invention:

Extrachromosomal element... a hereditary unit that is physically separate from the chromosome of the cell; the terms "extrachromosomal element" and "plasmid" are synonymous; when physically separated from the chromosome, some plasmids can be transmitted at high frequency to other cells, the transfer being without associated chromosomal transfer;

Episome... a class of plasmids that can exist in a state of integration into the chromosome of their host cell or as an autonomous, independently replicating, cytoplasmic inclusion;

Transmisible plasmid... a plasmid that carries genetic determinants for its own intercell transfer via conjugation;

DNA... deoxytribonucleic acid;

Bacteriophage... a particle composed of a piece of DNA encoded and contained within a protein head portion and having a tail and tail fibers composed of protein;

Transducing phage... a bacteriophage that carries fragments of bacterial chromosomal DNA and transfers this DNA on subsequent infection of another bacterium;

Conjugation... the process by which a bacterium establishes cellular contact with another bacterium and the transfer of genetic material occurs;

Curing... the process by which selective plasmids can be eliminated from the microorganism;

Curing agent... a chemical material or a physical treatment that enhances curing;

Genome... a combination of genes in some given sequence;

Degradative pathway... a sequence of enzymatic reactions (e.g. 5 to 10 enzymes are produced by the microbe) converting the primary substrate to some simple common metabolite, a normal food substance for microorganisms;

(Sole carbon source)$^-$... indicative of a mutant incapable of growing on the given sole carbon source;

(Plasmid)$^{del}$... indicative of cells from which the given plasmid has been completely driven out by curing or in which no portion of the plasmid ever existed;

(Plasmid)$^-$... indicative of cells lacking in the given plasmid; or cells harboring a non-functional derivative of the given plasmid;

(Amino-acid)$^-$... indicative of a strain that cannot manufacture the given amino acid;

(Vitamin)$^-$... indicative of a strain that cannot manufacture the given vitamin and (Plasmid)$^+$... indicates that the cells contain the given plasmid.

Plasmids are believed to consist of double-stranded DNA molecules. The genetic organization of a plasmid is believed to include at least one replication site and a maintenance site for attachment thereof to a structural component of the host cell. Generally, plasmids are not essential for cell viability.

Much work has been done supporting the existence, functions and genetic organization of plasmids. As is reported in the review by Richard P. Novick "Extrachromosomal Inheritance in Bacteria" (Bacteriological Reviews, June 1969, pp. 210-263, [1969]) on page 229, "DNA corresponding to a number of different plasmids has been isolated by various methods from plasmid-positive cells, characterized physiochemically and in some cases examined in the electron microscope".

There is no recognition in the Novick review of the existence of energy-generating plasmids specifying degradative pathways. As reported on page 237 of the Novick review, of the known (non energy-generating) plasmids "Combinations of four or five different plasmids in a cell seem to be stable."

Plasmids may be compatible (i.e. they can reside stably in the same host cell) or incompatible (i.e. they are unable to reside stably in a single cell). Among the known plasmids, for example, are sex factor plasmids and drug-resistance plasmids.

Also, as stated on page 240 of the Novick review, "Cells provide specific maintenance systems or sites for plasmids. It is though that attachment of such sites is required for replication and for segregation of replicas. Each plasmid is matched to a particular maintenance site...". Once a plasmid enters a given cell, if there is no maintenance site available, because of prior occupancy by another plasmid, these plasmids will be incompatible.

The biodegradation of aromatic hydrocarbons such as phenol, cresols and salicylate has been studied rather extensively with emphasis on the biochemistry of these processes, notably enzyme characterization, nature of intermediates involved and the regulatory aspects of the enzymic actions. The genetic basis of such biodegradation, on the other hand, has not been as thoroughly studied because of the lack of suitable transducing phages and other genetic tools.

The work of Chakrabarty and Gunsalus (Genetics, 68, No. 1, page S10, [1971]) has showed that the genes governing the synthesis of the enzymes responsible for the degradation of camphor constitute a plasmid. Similarly, this work has shown the plasmid nature of the octane-degradative pathway. However, attempts by the authors to provide a microorganism with both CAM and OCT plasmids were unsuccessful, these plasmids being incompatible.

In *Escherichia coli* artificial, transmissible plasmids (one per cell) have been made, each containing a degradative pathway. These plasmids, not naturally occurring, are F'lac and F'gal, wherein the lactose-and galactose-degrading genes were derived from the chromosome of the organism. Such plasmids are described in "F-prime Factor Formation in *E. Coli* K12" by J. Scaife (Genet. Res. Cambr. [1966], 8, pp. 189-196).

If the development of microorganisms containing multiple containing energy-generating plasmids specifying preselected degradative pathways could be made possible, the economic and environmental impact of such an invention would be vast. For example, there would be immediate application for such versatile microbes in the production of proteins from hydrocarbons ("Proteins from Petroleum"—Wang, Chemical Engineering, August 26, 1968, page 99); in cleaning up oil spills ("Oil Spills: An Environmental Threat"—Environmental Sciene and Technology, Volume 4, February 1970, page 97); and in the disposal of used automotive lubricating oils ("Waste Lube Oils Pose Disposal Dilemma", Environmental Science and Technology, Volume 6, page 25, January 1972).

SUMMARY OF THE INVENTION

A transmissible plasmid has been found that specifies a degradative pathway for salicylate [SAL], an aromatic hydrocarbon. In addition, a plasmid has been identified that specifies a degradative pathway for naphthalene [NPL], a polynuclear aromatic hydrocarbon. The NPL plasmid is also transmissible.

Having established the existence of (and transmissibility of) plasmid-borne capabilities for specifying separate degradative pathways for salicylate and naphthalene, unique single-cell microbes have been developed containing various stable combinations of the [CAM], [OCT], [SAL], and [NPL] plasmids. In addition, stable combinations in a single cell of the aforementioned plasmids together with a non energy-generating plasmid [drug resistance factor RP-1] have been achieved. The versatility of these novel microorganisms has been demonstrated by the substantial extent to which degradation of such complex hydrocarbons as crude oil and Bunker C oil has been achieved thereby.

BRIEF DESCRIPTION OF THE DRAWING

The exact nature of the invention as well as objects and advantages thereof will be readily apparent from consideration of the following specification relating to the annexed drawing in which.

DESCRIPTION OF THE PREFERRED EMBODIMENT

Figure 1:
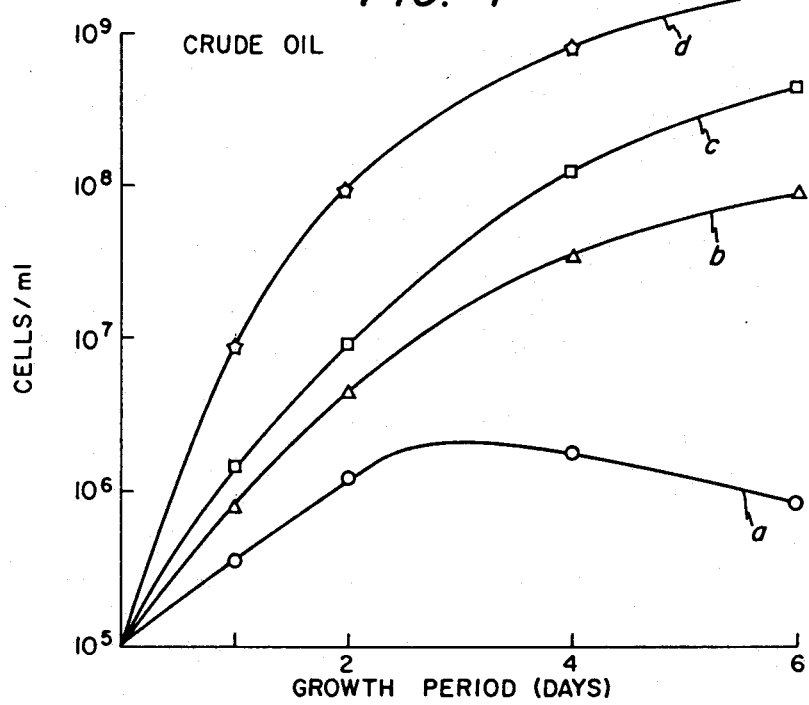
FIG. 1 shows the increase in growth rate in crude oil of Pseudomonas strain bacteria provided with increasing numbers of energy-generating degradative plasmids by the practice of this invention and FIG. 2 shows the increase in growth rate in Bunker C oil of Pseudomonas strain bacteria provided with increasing numbers of energy-generating degradative plasmids by the practice of this invention.

Microorganisms prepared by the genetic engineering processes described herein are exemplified by cultures now on deposit with the U.S. Department of Agriculture. These cultures are identified as follows:

*Pseudomonas aeruginosa* (NRRL B-5472) . . . derived from *Pseudomonas aeruginosa* strain 1c (ATCC No. 15692) by genetic transfer thereto, and containment therein, of camphor, octane, salicylate and naphthalene degradative pathways in the form of plasmids.

*Pseudomonas putida* (NRRL B-5473) . . . derived from *Pseudomonas putida* strain PpGl (ATCC No. 17453) by genetic transfer thereto, and containment therein, of camphor, salicylate and naphthalene degradative pathways and a drug resistance factor RP-1, all in the form of plasmids. The drug resistance factor is responsible for resistance to neomycin/kanamycin, carbenicillin and tetracycline.

A sub-culture of each of these strains can be obtained from the permanent collection of the Northern Marketing and Nutrient Research Division, Agricultural Service, U.S. Department of Agriculture, Peoria, IL, U.S.A.

Morphological observations in various media, growth in various media, general group characterization tests, utilization of sugars and optimum growth conditions for the strains from which the above-identified organisms were derived are set forth in "The Aerobic Pseudomonads: A Taxonomic Study" by Stanier, R. Y. et al [Journal of General Microbiology 43, pp. 159–271 (1966)]. The taxonomic properties of the above-identified organisms remain the same as those of the parent strains.

P. aeruginosa strain 1c (ATCC No. 15692) is the same as strain 131 (ATCC No. 17503) in the Stanier et al study. Later the designation for this strain was changed to *P. aeruginosa* PAO [Holloway, B. W. "Genetics of Pseudomonas", Bacteriological Reviews, 33, 419–443 (1969)]. *P. putida* strain PpGl (ATCC No. 17453) is the same as strain 77 (ATCC No. 17453) in the Stanier et al study.

As will be described in more detail hereinbelow, these organisms thrive on a very wide range of hydrocarbons including crude oil and Bunker C oil. These organisms are non-pathogenic as is the general case with laboratory strains of Pseudomonas.

In brief, the process for preparing microbes containing multiple compatible energy-generating plasmids specifying separate degradative pathways is as follows:

(1) selecting the complex or mixture to be degraded;

(2) identifying the plurality of degradative pathways required in a single cell to degrade the several components of the complex or mixture therewith;

(3) isolating a strain of some given microorganism on one particular selective substrate identical or similar to one of the several components (the selection of the microorganism is generally on the basis of a demonstrated superior growth capability);

(4) determining whether the capability of the given strain to degrade the selective substrate is plasmid-borne;

(5) attempting to transfer this first degradative pathway by conjugation to other strains of the same organism (or to the same strain which has been cured of the pathway) and then verifying the transmissible nature of the plasmid;

(6) purifying the conjugatants (recipients of the plasmids by conjugation) and checking for distinctive characteristics of the recipient to insure that the recipient did, in fact, receive the degradative pathway;

(7) repeating the process so as to introduce a second plasmid to the conjugatants;

(8) rendering the first and second plasmids compatible, if necessary, by fusion of the plasmids and (9) repeating the process as outlined above until the full complement of degradative pathways desired in a single cell has been accomplished by plasmid transfer (and fusion, when required).

In the first reported instance (Chakrabarty et al article mentioned hereinabove) in which the attempt was made to locate more than one energy-generating degradative pathway in the same cell, it was found that CAM and OCT plasmids cannot exist stably under these conditions. In spite of the implication from these results that multiple energy-generating plasmid content in a single cell could be achieved but not maintained, it was decided to attempt to discover some way in which to overcome this problem of plasmid incompatibility. As noted hereinabove and described more fully hereinbelow with specific reference to energy-generating plasmid transfer in the genus Pseudomonas, the problem of plasmid instability has now been solved by bringing about fusion of the plasmids in the recipient cell.

The development of single cell capability for the degradation and conversion of complex hydrocarbons was selected as the immediate beneficial application with particular emphasis on the genetic control of oil spills by the way of a single strain of Pseudomonas. In order to be able to cope with crude oil and Bunker C oil spills it was decided that the single cells of Pseudomonas derivate produced by this invention should possess degradative pathways for linear aliphatic, cyclic aliphatic, aromatic and polynuclear aromatic hydrocarbons. *Pseudomonas aeruginosa* (NRRL B-5472) strain, which displays these degradative capabilities was thereupon eventually developed.

Massive oil spills that are not promptly contained and cleaned up have a catastrophic effect on aquatic lives. Microbial strains are known that can decompose individual components of crude oil (thus, various yeasts can degrade aliphatic straight-chain hydrocarbons, but not most of the aromatic and polynuclear hydrocarbons). Pseudomonas and other bacteria species are known to degrade the aliphatic, aromatic and polynuclear aromatic hydrocarbon compounds, but, unfortunately any given strain can degrade only a particular component. For this reason, prior to the instant invention, biological control of oil spills had involved the use of a mixture of bacterial strains, each capable of degrading a single component of the oil complex on the theory that the cumulative degradative actions would consume the oil and convert it to cell mass. This cell mass in turn serves as food for aquatic life. However, since bacterial strains differ from one another in (a) their rates of growth on the various hydrocarbon components, (b) nutritional requirements, production of antibiotics or other toxic material, and (c) requisite pH, temperature and mineral salts, the use of a mixed culture leads to the ultimate survival of but a portion of the initial collection of bacterial strains. As a result, when a mixed culture of hydrocarbon-degrading bacteria are deposited on an oil spill the bulk of the oil often remains unattacked for a long period of time (weeks) and is free to spread or sink.

By establishing that SAL and NPL degradative pathways are specified by genes borne by transmissible plasmids in Pseudomonas and by the discovery that plasmids can be rendered stable (e.g. CAM and OCT) by fusion of the plasmids it has been made possible, for the first time, to genetically engineer a strain of Pseudomonas having the single cell capability for multiple separate degradative pathways. Such a strain of microbes equipped to simultaneously degrade several components of crude oil can degrade an oil spill much more quickly (days) than a mixed culture meanwhile bringing about coalescence of the remaining portions into large drops. This action quickly removes the opportunity for spreading of the oil thereby enhancing recovery of the coalesced residue.

Preparation of *P. aeruginosa* [NRRL B-5472]

The compositions of the synthetic mineral media for growth of the cultures were the same for all the Pseudomonas species employed. The mineral medium was prepared from:

PA Concentrate . . .
  100 ml of 1 Molar $K_2HPO_4$
  50 ml of 1 Molar $KH_2PO_4$
  160 ml of 1 Molar $NH_4Cl$
100×Salts . . .
  19.5 gm $MgSO_4$
  5.0 gm $MnSO_4 \cdot H_2O$
  5.0 gm $FeSO_4 \cdot 7H_2O$
  0.3 gm $CaCl_2 \cdot 2H_2O$
  1.0 gm Ascorbic acid
  1 liter $H_2O$ Each of the above (PA Concentrate and 100×Salts) was sterilized by autoclaving. Thereafter, one liter of the mineral medium was prepared as follows:

| | |
|---|---|
| PA Concentrate | 77.5 ml |
| 100 X Salts | 10.0 ml |
| Agar | 15.0 gm |
| $H_2O$ | to one liter (The pH is adjusted to 6.8–7.0). |

All experiments were carried out at 32° C. unless otherwise stated.

It was decided that a very useful hydrocarbon degradation capability would be attained in a single *Pseudomonas aeruginosa* cell, if the degradative pathways for linear aliphatic, cyclic aliphatic, aromatic and polynuclear aromatic hydrocarbons could be transferred thereto. *Pseudomonas aeruginosa* PAO was selected because of its high growth rate even at temperatures as high as 45° C. Four strains of Pseudomonas were selected having the individual capabilities for degrading n-octane (a linear aliphatic hydrocarbon), camphor (a cyclic aliphatic hydrocarbon), salicylate (an aromatic hydrocarbon) and naphthalene (a polynuclear aromatic hydrocarbon).

The specific strains of Pseudomonas able to degrade these hydrocarbons were then treated with curing agent to verify the plasmid-nature of each of these degradative pathways. Of the known curing agents (e.g. sodium dodecyl sulfate, urea, acriflavin, rifampicin, ethidium bromide, high temperature, mitomycin C, acridine orange etc.) most were unable to cure any of the degradative pathways. However, it was found (Table I) that the degradative pathways of the several species could be cured with mitomycin C. Each of the Pseudomonas strains bearing the specified degradative pathways are known in the art:

| | | |
|---|---|---|
| (a) | $CAM^+$ *P. putida* PpG1 | Proc. Nat. Acad. Sci. (U.S.A.), 60, 168 (1968) |
| (b) | $OCT^+$ *P. oleovorans* | J. Biol. Chem. 242, 4334 (1967) |
| (c) | $SAL^+$ *P. putida* R-1 | Bacteriological Proceedings 1972 p. 60 |
| (d) | $NPL^+$ *P. aeruginosa* | Biochem. J. 91, 251 (1964) |

TABLE I

| Strain | Degradative Pathway | Mitomycin C Concentration (μg/ml) | Frequency of Curing (Percent) |
|---|---|---|---|
| CAM⁺ *P. putida* PpG1 | cyclic aliphatic hydrocarbon (camphor) | 0 | <0.01 |
| | | 10 | 5 |
| | | 20 | 95 |
| OCT⁺ *P. oleovorans* | aliphatic hydrocarbon (n-octane) | 0 | <0.1 |
| | | 10 | 1.0 |
| | | 20 | 3.0 |
| SAL⁺ *P. putida* R-1 | aromatic hydrocarbon | 0 | <0.1 |

TABLE I-continued

| Strain | Degradative Pathway | Mitomycin C Concentration ($\mu$g/ml) | Frequency of Curing (Percent) |
|---|---|---|---|
| | (salicylate) | 5 | 0.7 |
| | | 10 | 3.0 |
| | | 15 | 4.0 |
| NPL+ P. aeruginosa | polynuclear aromatic hydrocarbon | | |
| | (naphthalene) | 0 | <0.1 |
| | | 5 | 0.5 |
| | | 10 | 1.8 |

Curing degradative pathways from each strain with mitomycin C was accomplished by preparing several test tubes of L broth [Lennox E.S. (1955), Virology, 1, 190] containing varying concentrations of mitomycin C and inoculating these tubes with suitable dilutions of early stationary phase cells of the given strain to give concentrations $10^4$ to $10^5$ cells/ml. These tubes were incubated on a shaker at 32° C. for 2-3 days. Aliquots from tubes that showed some growth were then diluted and plated on glucose minimal plates. After growth at 32° C. for 24 hours, individual colonies were split and respotted on glucose-minimal and degradative pathway-minimal plates to give the proportion of $CAM^-$, $OCT^-$, $SAL^-$ and $NPL^-$ in order to determine the frequency of curing. It was, therefore, shown that in each instance the degradative pathway genes are plasmid-borne.

Transductional studies with a number of point mutants in the camphor and salicylate pathways has suggested that the cured segments lost either the entire or the major portion the plasmid genes. The plasmid nature of the degradative pathways was also confirmed from evidence of their transmissibility by conjugation from one strain to another (Table II). Although the frequency of plasmid transfer varies widely with individual plasmids and although OCT plasmid cannot be transferred from P. oleovorans to P. aeruginosa PAO at any detectable frequency, most of the plasmids can nevertheless be transferred from one strain to another by conjugation.

The plasmid transfers, instead of being made to other strains could have been made to organisms of the same strain, that had been cured of the given pathway with mitomycin C, acridine orange or other curing agent.

Pseudomonas putida U has been described in the article by Feist et al [J. Bacteriology 100, p. 869-877 (1969)].

The auxotropic mutants (mutants that require a food source containing a particular amino acid or vitamin for growth) shown in Table II as donors were each grown in a complex nutrient medium (e.g. L broth) to a population density of at least about $10^8$ cells/ml without shaking in a period of from 6 to 24 hours. The prototropic (cells capable of growing on some given minimal source of carbon) recipients to which degradative pathway transfer was desired were grown separately in the same complex nutrient medium to a population density of at least about $10^8$ cells/ml with shaking in a period of from 4 to 26 hours. For each degradative pathway transfer these cultures were mixed in equal volumes, kept for 15 minutes to 2 hours at 32° C. without shaking (to permit conjugation to occur) and then plated on minimal plates containing the particular substrate as the sole source of carbon. This procedure for cell growth of donor and recipient and the mixing thereof is typical of the manner in which conjugation and plasmid transfer is encouraged in the laboratory, this procedure being designed to provide a very efficient transfer system. Temperature is not critical, but the preferred temperature range is 30°-37° C. Reduction in the population density of either donor or recipient below about 1,000,000 cells/ml or any change in the optimal growth conditions (stationary growth of donor, agitated growth of recipient, growth in high nutrient content medium, harvest of recipient cells at log phase) will drastically reduce the frequency of plasmid transfer.

The details for preparing and isolating auxotropic mutants is described in the textbook, "The Genetics of Bacteria and Their Viruses" by William Hays [John Wiley & Sons, Inc. (1965)].

TABLE II

| Donor | Recipient | Degradative Pathway | Frequency of Transfer |
|---|---|---|---|
| Trp$^-$CAM$^+$ | P. aeruginosa PAO | CAM | $10^{-3}$ |
| P. putida PpG1 | CAM$^{del}$ P. putida | CAM | $10^{-2}$ |
| Met$^-$OCT$^+$ | P. aeruginosa PAO | OCT | $<10^{-9}$ |
| P. oleovorans | P. putida PpG1 | OCT | $10^{-9}$ |
| | P. putida U | OCT | $10^{-7}$ |
| His$^-$SAL$^+$ | P. aeruginosa PAO | SAL | $10^{-7}$ |
| P. putida R-1 | P. putida PpG1 | SAL | $10^{-6}$ |
| Trp$^-$NPL$^+$ | P. putida PpG1 | NPL | $10^{-7}$ |
| P. aeruginosa | NPL$^{del}$ P. aeruginosa PAO | NPL | $10^{-5}$ |

Abbreviations:
Trp - tryptophane
Met - methionine
His - histidine

Control cultures of donors and recipients were also plated individually on minimal plates containing the requisite substrate in each instance as the sole source of carbon, to determine the reversion frequency of donor and recipient cells.

All plates (including controls) were incubated at 30°-37° C. for several days. In each instance in which colonies appeared in numbers exceeding the colony growth on the reversion plates, it was established that degradative pathway transfer had occurred between the donors and recipients. Such conjugatants were than purified by a series of single colony isolation cultures and checked for growth rates or other distinctive characteristics of the recipient to insure that the recipient actually received the given degradative pathway.

Having determined that the degradative pathways were plasmid-borne and transmissible, the task of transferring the multiplicity of plasmids to a single cell P. aeruginosa PAO was undertaken. Prior work (referred to hereinabove) had established that OCT placmids could not be transferred from P. oleovorans to P. aeruginosa PAO. Therefore, the first task was to discover how (if at all) the OCT and CAM plasmids could be rendered compatible.

The CAM plasmid was transferred to a Met⁻ mutant of OCT⁺ P. oleovorans strain from a CAM⁺ P. putida strain. The conjugatant is, of course, unstable and will segregate either CAM or OCT at an appreciable rate. Therefore, the conjugatant was alternately grown in camphor and then octane as sole sources of carbon to isolate those cells in which both of these degradative pathways were present, even though unstable. The surviving cells were centrifuged, suspended in 0.9% saline solution and irradiated with UV rays (3 General Electric FS-5 lamps providing a total of about 24 watts). Aliquots were drawn from the suspension as follows: one aliquot was removed before UV treatment, one aliquot after UV exposure for 30 seconds and one aliquot after UV exposure for 60 seconds. These aliquots of irradiated cells were grown in the absence of light for 3 hours in L broth and were then used as donors for the transfer of plasmids to the P. aeruginosa PAO strain as recipient, selection being made for the OCT plasmid on an octane minimal plate.

As is shown in Table III aliquots of similarly irradiated suspensions for Met⁻OCT⁺CAM$^{del}$ P. oleovorans and Met⁻CAM⁺OCT$^{del}$ P. oleovorans were prepared and used as plasmid donors to P. aeruginosa PAO, selection being made for the plasmids shown. The Met⁻CAM⁺OCT$^{del}$ strain was prepared by introducing CAM plasmids into Met⁻OCT⁺ mutant of P. oleovorans and selecting for CAM⁺ conjugatants, which have lost the OCT plasmid. The Met⁻OCT⁺CAM$^{del}$ P. oleovorans is the Met⁻ mutant of wild type P. oleovorans.

The failure to secure determinable transfer of OCT plasmids from Met⁻OCT⁺ P. oleovorans to the recipient and the success in securing transfer of CAM plasmids from Met⁻CAM⁺OCt$^{del}$ P. oleovorans to the recipient are shown. These results support the theory that the successful transfer of OCT plasmids from the Met⁻CAM⁻OCT⁺ P. oleovorans (that had been irradiated for 30 seconds with UV rays) to P. aeruginosa PAO had been made possible by the fusion of the CAM and OCT plasmids in the P. oleovorans by the UV exposure and the subsequent transfer of CAM/OCT plasmids in combination (with separate degradative pathways), to the recipient.

mutant of CAM⁺OCT⁺ P. aeruginosa PAO that had been provided with its multiple plasmids by the methods described herein for plasmid transfer and plasmid fusion was used as the donor. After conjugation between the donor and OCT$^{del}$ CAM$^{del}$ P. putida PpGl, the resulting culture was plated on minimal plates containing camphor and also on minimal plates containing n-octane. Part of each of 132 colonies growing on the CAM minimal plates were transferred to OCT minimal plates and part of each of 219 colonies growing on the OCT minimal plates were transferred to CAM minimal plates. Each of these transferred portions grew, which tedns to establish that (a) both CAM and OCT plasmids had been transferred to the conjugatant, (b) the transfer had been on a one-for-one basis and, therefore, (c) the CAM and OCT plasmids were fused together.

Similar plasmid transfer was carried out between the Trp⁻CAM⁺OCT⁺P. aeruginosa PAO donor and OCT$^{del}$CAM$^{del}$ P. aeruginosa PAO and similar selection procedures were employed. The results further reinforced the above position as to the fused nature of the transferred CAM and OCT plasmids. When the CAM and OCT plasmids have been subjected to UV radiation as disclosed, if either CAM or OCT plasmid is transferred, the other plasmid will always be associated with it regardless of which plasmid is selected first. If either plasmid of the fused pair is cured from the cell, both plasmids are lost simultaneously. Thus, the conjugatants were treated with mitomycin C and the resultant CAM$^{del}$ segregants were examined. Invariably all CAM$^{del}$ segregants were found to have lost the OCT plasmid as well. Thus, the facts of simultaneous curing of the two plasmids and the co-transfer thereof strongly suggest that incompatible plasmids treated with means for cleaving the DNA of the plasmids results in fusion of the DNA segments to become part of the same replicon.

TABLE IV

| Donor | Recipient | Selected Plasmid | Non-selected Plasmid | Total OCT⁺/CAM⁺ |
|---|---|---|---|---|
| Trp⁻CAM⁺OCT⁺ | OCT$^{del}$CAM$^{del}$ | CAM | OCT | 132/132 |
| P. aeruginosa PAO | P. putida PpG1 | OCT | CAM | 219/219 |
|  | OCT$^{del}$CAM$^{del}$ | CAM | OCT | 107/107 |
|  | P. aeruginosa PAO | OCT | CAM | 96/96 |

Having successfully overcome all obstacles to the formation of a stable CAM⁺OCT⁺SAL⁺NPL⁺ Pseudomonas the several energy-generating degradative plasmids were transferred to a single cell as is shown in Table V by the conjugation techniques described hereinabove. The initial P. aeruginosa strain used is referred to herein as P. aeruginosa PAO, formerly known as P.

TABLE III

| Donor | Recipient | Selected Plasmid | Period of UV-Irradiation (Sec) | Transfer of Frequency |
|---|---|---|---|---|
| Met⁻OCT⁻ P. oleovorans | P. aeruginosa PAO | OCT | 0 | <10⁻⁹ |
|  |  |  | 30 | <10⁻⁹ |
|  |  |  | 60 | <10⁻⁹ |
| Met⁻CAM⁻OCT$^{del}$ P. oleovorans | P. aeruginosa PAO | CAM | 0 | 10⁻⁴ |
|  |  |  | 30 | 10⁻⁵ |
|  |  |  | 60 | 10⁻⁷ |
| Met⁻CAM⁻OCT⁻ P. oleovorans | P. aeruginosa PAO | OCT | 0 | <10⁻⁹ |
|  |  |  | 30 | 10⁻⁸ |
|  |  |  | 60 | <10⁻⁹ |

Table IV presents verification of this theory of co-transfer of CAM and OCT fused plasmids. A Trp⁻ aeruginosa strain 1c available as ATCC No. 15692 and- /ro ATCC No. 17503. This strain of *P. aeruginosa* does not contain any known energy-generating plasmid. The CAM and OCT plasmids exist in the fused state, are individually and simultaneously functional and appear perfectly compatible with the individual compatible SAL and NPL plasmids. Tests for compatibility of obth CAM+OCT+SAL+ *P. aeruginosa* PAO and CAM+OCT+SAL+NPL+ *P. aeruginosa* PAO revealed that there is no segregation of the plasmids in excess of that found in the donor. Plasmids will be accepted and maintained by *P. acidovorans*, *P. alcaligenes* and *P. fluorescens*. All of these plasmids should be transferable to and maintainable in these and many other species of Pseudomonas, such as *P. putida*, *P. oleovorans*, *P. multivorans*, etc.

Superstrains such as the CAM+OCT+SAL+NPL+ strain of *P. aeruginosa* PAO can grow on a minimal plate of any of camphor, n-octane, salicylate, naphthalene and, because of the phenomenon of relaxed specificity, on compounds similar thereto. Thus, the effectiveness of a given degradative plasmid does not appear to be diminished in its ability to function singly by the presence of other degradative plasmids in the same cell.

strains of *P. aeruginosa* PAO. Curve a shows the cell growth as a function of time of P. aeruginosa without any plasmid-borne energy-generating degradative pathways. Curve b shows greater cell growth as a function of time for SAL+ *P. aeruginosa*. Curve c shows still greater cell growth as a function of time for SAL+NPL+ *P. aeruginosa*. Curve d shows cell growth that is significantly greater still as a function of time for the CAM+OCT+SAL+NPL+ superstrain of *P. aeruginosa*. These results clearly establish that cells artifically provided by the practice of this invention with the genetic capability for degrading different hydrocarbons can grow at a faster rate and better on crude oil as the plasmid-borne degradative pathways are increased in number and variety, because of the facility of these degradative pathways to simultaneously function at full capacity.

Figure 2:
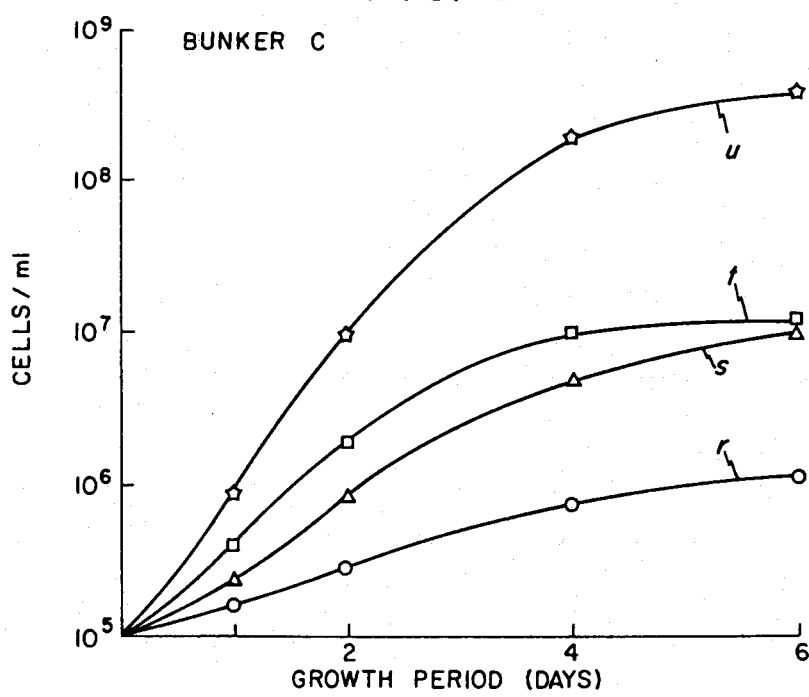

Similar results are shown in FIG. 2 displaying the growth capabilities of this same series of organisms utilizing Bunker C oil as the sole source of carbon. Bunker C is (or is prepared from) the residuum remaining after the more commercially useful components have been removed from crude oil. This residuum is

TABLE V

| Donor | Recipient | Selected Plasmid | Phenotype of the Conjugatant |
|---|---|---|---|
| Trp⁻CAM+OCT+ *P. aeruginosa* PAO | *P. aeruginosa* PAO | CAM | CAM+OCT+ *P. aeruginosa* PAO |
| His⁻SAL+ *P. putida* R-1 | CAM+OCT+ *P. aeruginosa* PAO | SAL | CAM+OCT+SAL+ *P. aeruginosa* PAO |
| Trp⁻NPL+ *P. aeruginosa* | CAM+OCT+SAL+ *P. aeruginosa* PAO | NPL | CAM+OCT+SAL+NPL+ *P. aeruginosa* PAO |

Indication of the capability of all degradative plasmids to function simultaneously in energy generation is provided by tests in which CAM+OCT+SAL+NPL+ *P. aeruginosa* PAO superstrain was added to separate broth samples each of which contained 1 millimolar (mM) of nutrient (a suboptimal concentration), one set of samples containing camphor, a second set of samples containing n-octane, a third set of samples containing salicylate and a fourth set of samples containing naphthalene, these being the sole sources of carbon in each instance. The superstrain grew very slowly in the separate sole carbon source samples. However, when the superstrain was added to samples containing all four sources of carbon present together in the same (1 mM)

very thick and sticky and without significant use, per se. A small amount of volatile hydrocarbons is often added thereto to lower the viscosity. Curve r reflects the cell growth as a function of time of *P. aeruginosa* cells not having any plasmid-borne energy-degradative pathways. Curve s shows increased cell growth as a function of time for SAL+ *P. aeruginosa*. Curve t shows further increase in cell growth as a function of time for SAL+NPL+ *P. aeruginosa*. Curve u shows still more significant cell growth as a function of time for CAM+OCT+SAL+NPL+ *P. aeruginosa*.

The SAL+ *P. aeruginosa* and SAL+NPL+ *P. aeruginosa* cultures were prepared as shown in Table VI below:

TABLE VI

| Donor | Recipient | Selected Plasmid | Conjugatant |
|---|---|---|---|
| His SAL+ *P. putida* R-1 | *P. aeruginosa* PAO | SAL | SAL+ *P. aeruginosa* PAO |
| Trp⁻NPL+ *P. aeruginosa* | SAL+ *P. aeruginosa* PAO | NPL | SAL+NPL+ *P. aeruginosa* PAO | concentration of 4 mM, the rate of growth increased considerably establishing that simultaneous utilization of all four sources of carbon had occurred.

Next, the ability of such superstrains to degrade crude oil was demonstrated. Crude oils, of course, vary greatly (depending upon source, period of activity of the well, etc.) in the relative amounts of linear aliphatic, cyclic aliphatic, aromatic and polynuclear hydrocarbons present, although some of each of these classes of hydrocarbons is typically present in some amount in the chemical make up of all crude oils from producing wells.

FIG. 1 shows the difference in growth capabilities in crude oil as the sole source of carbon of four single cell The experiments providing the data for FIGS. 1 and 2 were conducted in 250 ml Erlenmeyer flasks. To each flask was added 50 ml of mineral medium (described hereinabove) with pH adjusted to 6.8-7.0; 2.5 ml of the sole carbon source (crude oil or Bunker C) and $5 \times 10^6 - 1 \times 10^7$ cells. Growth was conducted at 32° C. with shaking. At daily intervals 5 ml aliquots were taken. The optical densities of these aliquots were determined at 660 nm in a Bausch & Lomb, Inc. colorimeter to determine organism density. Also, viable cell counts were determined by diluting portions of the aliquots and plating on L-agar (L-broth containing agar) plates. The colonies were counted after 24 hours of incubation at 32° C. and these counts were used to construct FIGS. 1 and 2. Also, the cells were submitted to protein analysis, to be discussed hereinbelow.

The 2.5 ml of crude oil or Bunker C appears to have initially offered an essentially unlimited food supply, but the results shown may well represent less than the full capability of the superstrain, because the relative amounts of the various hydrocarbons (degradable by the CAM+, OCT+, SAL+ and NPL+ plasmids) present in the carbon sources had not been ascertained and after a couple of days the food supply for one or more plasmids may have been limited.

A very significant aspect of the growth of the superstrain in crude and Bunker C oils is the fact that the components, which would spread the quickest on the water's surface from spills of these oils, disappear within 2-3 days and the remaining components of the oil coalesce to form large droplets that cannot spread out. These droplets can be removed more easily by mechanical recovery techniques as the microbes continue to consume these remaining components.

In practice an inoculum of dry (or lyophilized) powders of these genetically engineered microbes will be dispersed over (e.g. from overhead) an oil spill as soon as possible to control spreading of the oil, which is so destructive of marine flora and fauna and the microbes will degrade as much of the oil as possible to reduce the amount that need be recovered mechanically, when equipment has reached the scene and has been rendered operative. A particularly beneficial manner of depositing the inoculum on the oil spill is to impregnate straw with the inoculum and drop the inoculated straw on the oil spill where both components will be put to use—the inoculum (mass of microbes) to degrade the oil and the straw to act as a carrier for the microbes and also to function as an oil absorbent. Other absorbent materials may be used, if desired, but straw is the most practical. No special care need be taken in the preparation and storage of the dried inoculum or straw (or other absorbent material) coated with inoculum. No additional nutrient or mineral content need be supplied. Also, although culture from the logarithmic growth phase is preferred, culture from either the early stationary or logarithmic growth phases can be used.

It is reasonable to expect that a vast number of plasmid-borne hydrocarbon degradative pathways remain undiscovered. Hopefully, now that a method for controlled genetic additions to the natural degradative capabilities of microbes has been demonstrated by this invention, still more new and useful single cell organisms can be prepared able to degrade even more of the large number of hydrocarbons in crude oil, whether or not the plasmids yet to be found are compatible with each other or with those plasmids present in superstrains NRRL B-5472 and NRRL B-5473.

Both of these superstrains can be used as recipients for more plasmids. The capability for utilizing fusion (by UV irradiation or X-ray exposure) to render additional plasmids compatible is actually increased in a multiplasmid conjugatant, because of the larger selection of stable plasmids to which the newly introduced plasmid can be fused.

Preparation of P. putida [NRRL B-5473]

The mineral medium and the technique for fostering conjugation was the same as described above. A culture of antibiotic-sensitive P. putida PpG1 was cured of its CAM plasmids with mitomycin C and was used as the initial recipient. This strain of P. putida is sensitive to small (e.g. 25 micrograms/ml) concentrations of neomycin/kanamycin, carbenicillin and tetracycline. As is shown in Table VII below, all the donor strains are auxotropic mutants, because the use of auxotropic mutant donors facilitates counterselection of the conjugatants due to the ease of selecting against such donors.

TABLE VII

| Donor | Recipient | Selected Plasmid | Phenotype of the Conjugatant |
| --- | --- | --- | --- |
| Trp CAM· P. putida PpG1 | CAM$^{del}$ P. putida PpG1 | CAM | CAM+ P. putida PpG1 |
| His SAL· P. putida R-1 | CAM+ P. putida PpG1 | SAL | CAM+SAL+ P. putida PpG1 |
| Trp NPL· P. aeruginosa | CAM+SAL+ P. putida PpG1 | NPL | CAM+SAL+NPL+ P. putida PpG1 |
| Met P. aeruginosa Strain 1822 (RP-1) | CAM+SAL+NPL+ P. putida PpG1 | RP-1 | CAM+SAL+NPL+RP-1+ P. putida PpG1 |

The P. aeruginosa RP-1 strain is disclosed in the Sykes et al article [Nature 226, 952 (1970)]. Selection for the RP-1 plasmid was accomplished on a neomycin/kanamycin plate. Further, CAM+SAL+NPL+RP-1+ P. putida PpG1 has been determined to be resistant to carbenicillin and tetracycline establishing that the RP-1 plasmid is actually present and that the organisms that survived the selection process were not merely the results of mutant development. Also, the plasmids of this superstrain can be transferred and can be cured. The rate of segregation (spontaneous loss) of plasmids from the superstrain has been found to be the same as in the donors.

Both superstrains can, of course, be used as a source of plasmids in addition to those sources disclosed herein. For example, to transfer CAM, SAL or NPL plasmids from CAM+SAL+NPL+RP-1+ P. putida PpG1 to a given Pseudomonas recipient, the procedures for cell growth of donor and recipient and the mixing thereof for optimized conjugation is the same as described hereinabove. These plasmids will have different frequencies of transfer at different times. The order of diminishing frequency of transfer is CAM, NPL, SAL. For the transfer of CAM plasmid, after conjugation, selection is made for CAM. Surviving colonies are subdivided and selection is made for SAL, NPL and CAM plasmids from each colony. Those portions surviving only on camphor as the sole source of carbon will have received the CAM plasmid free of the SAL or NPL plasmids. The same procedure can be followed for the individual transfer of SAL or NPL plasmids.

In addition to the previously discussed capability for improved treatment of oil spills, considerable improvement is now possible in the microbial single-cell synthesis of proteins from carbon-containing substrates. The restriction of having to employ substantially single-component substrates, e.g. alkanes, paraffins, carbohydrates, etc. has now been removed, simultaneously providing the opportunity for increases of 50-100 fold in the amount of cell mass that may be produced by a single cell in a given time period, when the given single cell has been provided with multiple energy-generating plasmids. Also, being able to optimize the protein production of bacteria is of particular interest since bacterial cell mass has a much greater protein content and most bacteria have greater tolerance for heat than yeasts. This latter aspect is of importance since less refrigeration is necessary to remove the heat generated by the oxidative degradation of the substrate.

The general process and apparatus for single cell production of protein is set forth in the Wang article (incorporated by reference) referred to hereinabove. One particular advantage of the multi-plasmid single cell organism of this invention is that after the cell mass has been harvested it can be subjected to a subsequent incubation period in a mineral medium free of any carbon source for a sufficient period of time to insure the metabolism of residual intra-cellular hydrocarbons, e.g. polynuclear aromatics, which are frequently carcinogenic. Presently, treatment of cell mass to remove unattacked hydrocarbons often leads to reduction in the quality of the protein product.

The economics of protein production by single-cell organisms will be further improved by the practice of this invention, because of the reduced cost of substrate (e.g. oil refinery residue, waste lubricating oil, crude oil) utilizable by organisms provided with preselected plasmid content.

Cell mass growth in crude oil using NRRL B-5472 was harvested by centrifugation, washed two times in water and dried by blowing air (55° C.) over the mass overnight. The dried mass was hydrolyzed and analyzed for amino acid content by the technique described "High Recovery of Tryptophane from Acid Hydrolysis of Proteins"-Matsubara et al [Biochem. and Biophys. Res. Comm. 35 No. 2, 175-181 (1969)]. The amino acid analysis showed that the amino acid distribution of superstrain cell mass grown in crude oil is comparable to beef in threonine, valine, cystine, methionine, isoleucine, leucine, phenylalanine and tryptophane content and significantly superior to yeast in methionine content.

Continued capacity for increasing the degrading capability of the superstrains now on deposit has been made possible by the practice of this invention as more plasmid-borne degradative pathways are discovered. To date P. aeruginosa strain 1822 has been provided with all four known hydrocarbon degradative pathways (OCT, CAM, SAL, NPL) plus the drug-resistance factor RP-1 found therein. If there is an upper limit to the number of energy-generating plasmids that will be received and maintained in a single cell, this limit is yet to be reached. Attempts to integrate plasmids (CAM, OCT, SAL) with the cell chromosome have been unsuccessful as indicated by failure to mobilize the chromosome. Such results have so far verified the extrachromosomal nature of the energy-generating and drug-resistance plasmids. There is, of course, no reason to expect that the only plasmids are those that specify degradative pathways for hydrocarbons. Conceivably plasmids may be discovered that will provide requisite enzyme series for the degradation of environmental pollutants such as insecticides, pesticides, plastics and other inert compounds.

Energy-generating plasmids in general are known to have broad inducer and substrate specificity [i.e. enzymes will be formed and will act on a variety of structurally similar compounds]. For example, the CAM plasmid is known to have a very relaxed inducer and substrate specificity [Gunsalus et al-Israel J. Med. Sci., 1, 1099-1119 (1965) and Hartline et al-Journal of Bacteriology, 106, 468-478 (1971)]. Similarly, the OCT plasmid has broad inducer and substrate specificity [Peterson et al-J. Biol. Chem. 242, 4334 (1967)]. In the practice of the instant invention it has been demonstrated that plasmids display the same degree of relaxed specificity in the conjugatant as in the donor.

Thus, by the practice of this invention new facility and capability for growth has been embodied in useful single-cell organisms by the manipulation of phenomena that had been previously undiscovered (i.e. the plasmid-borne nature of the degradative pathways for salicylate and naphthalene) and/or had been previously unsuccessfully applied (i.e. rendering stable a plurality of previously incompatible plasmids in the same single cell).

Filed concurrently herewith is U.S. Application Ser. No. 260,488-Chakrabarty, filed June 7, 1972 now U.S. Pat. No. 3,814,474 and assigned to the assignee of the instant invention.

What I claim as new and desire to secure by Letters Patent of the United States is:

1. A bacterium from the genus Pseudomonas containing therein at least two stable energy-generating plasmids, each of said plasmids providing a separate hydrocarbon degradative pathway.

2. The Pseudomonas bacterium of claim 1 wherein the hydrocarbon degradative pathways are selected from the group consisting of linear aliphatic, cyclic aliphatic, aromatic and polynuclear aromatic.

3. The Pseudomonas bacterium of claim 1, said bacterium being of the specie P. aeruginosa.

4. The P. aeruginosa bacterium of claim 3 wherein the bacterium contains CAM, OCT, SAL and NPL plasmids.

5. The Pseudomonas bacterium of claim 1, said bacterium being of the specie P. putida.

6. The P. putida bacterium of claim 5 wherein the bacterium contains CAM, SAL, NPL and RP-1 plasmids.

7. An inoculum for the degradation of a preselected substrate comprising a complex or mixture of hydrocarbons, said inoculum consisting essentially of bacteria of the genus Pseudomonas at least some of which contain at least two stable energy-generating plasmids, each of said plasmids providing a separate hydrocarbon degradative pathway.

8. The inoculum of claim 7 wherein the hydrocarbon degradative pathways are selected from the group consisting of linear aliphatic, cyclic aliphatic, aromatic and polynuclear aromatic.

9. The inoculum of claim 8 wherein the bacteria having multiple energy-generating plasmids are of the specie P. aeruginosa.

10. The inoculum of claim 8 wherein the bacteria having multiple energy-generating plasmids are of the specie P. putida.

11. In the process in which a first energy-generating plasmid specifying a degradative pathway is transferred by conjugation from a donor Pseudomonas bacterium to a recipient Pseudomonas bacterium containing at least one energy-generating plasmid that is incompatible with said first plasmid, said transfer occurring in the quiescent state after the mixing of substantially equal volumes of cultures of said donor and said recipient, each culture presenting the respective organisms in a complex nutrient liquid medium at a population density of at least about 1,000,000 cells/ml, the improvement wherein after conjugation has occurred, the multi-plasmid conjugatant bacteria are subjected to DNA-cleaving radiation in a dosage sufficient to fuse the first plasmid and the plasmid incompatible therewith located in the same cell.

12. The improvement of claim 11 wherein the DNA-cleaving radiation is UV radiation.

13. The improvement of claim 12 wherein the first plasmid provides the degradative pathway for camphor and the recipient Pseudomonas contains the degradative pathway for n-octane.

14. An inoculated medium for the degradation of liquid hydrocarbon substrate material floating on water, said inoculated medium comprising a carrier material able to float on water and bacteria *from the genus Pseudomonas* carried thereby, at least some of said bacteria *each* containing at least two stable energy-generating plasmids, each of said plasmids providing a separate hydrocarbon degradative pathway and said carrier material being able to absorb said hydrocarbon material.

15. The inoculated medium of claim 14 wherein the carrier material is straw.

16. The inoculated medium of claim 14 wherein the hydrocarbon degradative pathways are selected from the group consisting of linear aliphatic, cyclic aliphatic, aromatic and polynuclear aromatic.

17. The inoculated medium of claim 14 wherein the bacteria are of the specie *P. aeruginosa*.

18. The inoculated medium of claim 14 wherein the bacteria are of the specie *P. putida*.